United States Patent [19]
Pierson, III et al.

[11] Patent Number: 5,797,915
[45] Date of Patent: Aug. 25, 1998

[54] CERCLAGE SYSTEM

[76] Inventors: Raymond H. Pierson, III, 62 Columbia St., Suite 102, Orlando, Fla. 32806; Thomas Wade Fallin, 819 Striker Ave., Suite 10, Sacramento, Calif. 95834-1129

[21] Appl. No.: 633,619

[22] Filed: Apr. 17, 1996

[51] Int. Cl.[6] .................................................. A61B 17/82
[52] U.S. Cl. ........................................ 606/74; 606/103
[58] Field of Search .......................... 606/74, 72, 103, 606/86, 60, 61, 232

[56] References Cited

U.S. PATENT DOCUMENTS

| | | | |
|---|---|---|---|
| 2,455,609 | 12/1948 | Scheib | 606/103 |
| 3,507,270 | 4/1970 | Ferrier | 606/74 |
| 5,127,413 | 7/1992 | Ebert | 128/898 |
| 5,536,270 | 7/1996 | Songer et al. | 606/74 |
| 5,545,168 | 8/1996 | Burke | 606/74 |

*Primary Examiner*—Guy V. Tucker
*Attorney, Agent, or Firm*—Snell & Wilmer L.L.P.

[57] ABSTRACT

A cerclage cable system comprises a cable in conjunction with a biasing mechanism for maintaining cable tension. Inadvertent loss of cable tension is compensated for by the biasing mechanism. In one embodiment, cerclage cable system includes a leaf spring disposed between the cable and the bone. Alternative embodiments include other biasing mechanisms, such as helical compression springs and resilient materials. Further embodiments include biasing mechanisms in line with the cable to maintain tension. Such a cerclage system maintains cable tension by taking up inadvertent slack in the cable with the biasing mechanism.

28 Claims, 7 Drawing Sheets

CERCLAGE SYSTEM

BACKGROUND OF THE INVENTION

1. Field of the Invention

The invention generally relates to surgical implements, and more particularly, to cerclage cable tensioning and retaining systems.

2. Description of the Related Art

Cerclage fixation of skeletal structures is an important procedure for orthopedic surgeons. Surgeons use cerclage systems in a variety of applications, including spine fusions, hip arthroplasty, fracture fixation, sternum closures, and the like. Typically, cerclage systems include a wire, cable, or suture wrapped tightly around the relevant bone and fixed in place. The cable usually comprises a wire or cable of biocompatible material, which is fixed in place by either twisting the free ends together or applying a retainer after an appropriate amount of tension has been placed on the wire or cable. The most common retainer is a sleeve which is crimped onto the wire or cable.

Achieving the appropriate tension in the cable is vital to the proper functioning of the cerclage system. For example, excessive tension in the cable can cause cable failure, bone fracture, or avascular necrosis of the bone around which the cable is wound. On the other hand, insufficient tensioning prevents the system from performing properly; sufficient tension must be maintained for proper fixation. Furthermore, the tensioning process is often difficult due to the small components and the high tensions required.

Various systems are available for applying and measuring cable tension. For example, both the Howmedica Dall Miles System and DePuy Control Cable System offer force multiplying pliers to apply and measure cable tension. To facilitate cable tension measurement, the Howmedica system uses a beam deflection torque wrench connected to the drive mechanism of the pliers, and the DePuy system uses a tension gauge built into the tensioning pliers. Each of these systems, however, only measures tension before the cable is secured. After securing the cable, for example by crimping a cable retainer, cable tension frequently decreases dramatically due to inadvertent oblique loading during the crimping process. In addition, after the implantation of the cerclage system, post-operative shifting of bone fragments and slippage of the cable in the securing mechanism may also contribute to loss of cable tension.

SUMMARY OF THE INVENTION

A cerclage cable system according to various aspects of the present invention provides a cerclage system dynamically tensioned to maintain high tension in the cerclage cable despite bone shifting, cable slippage, or other inadvertent loss of cable tension. In particular, an exemplary embodiment of a cerclage system includes a dynamically tensioning cable retainer which provides a bias to maintain tension in the cable after installation. The retainer includes a retaining mechanism, such as a crimp block, for retaining the cable and a biasing mechanism between the crimp block and the bone. In the event of cable slippage or slackening, the biasing mechanism tends to bias the cable away from the bone. Alternatively, a biasing mechanism may be connected in line with the cerclage cable, tending to bias the cable to maintain tension. As a result, cable tension is maintained regardless of inadvertent cable slackening after installation.

BRIEF DESCRIPTION OF THE DRAWING

The subject matter of the present invention is particularly pointed out and distinctly claimed in the concluding portion of the specification. The invention, however, both as to organization and method of operation, may best be understood by reference to the following description taken in conjunction with the claims and the accompanying drawing, in which like designations denote like elements and:

DETAILED DESCRIPTION OF PREFERRED EXEMPLARY EMBODIMENTS

Figure 1:
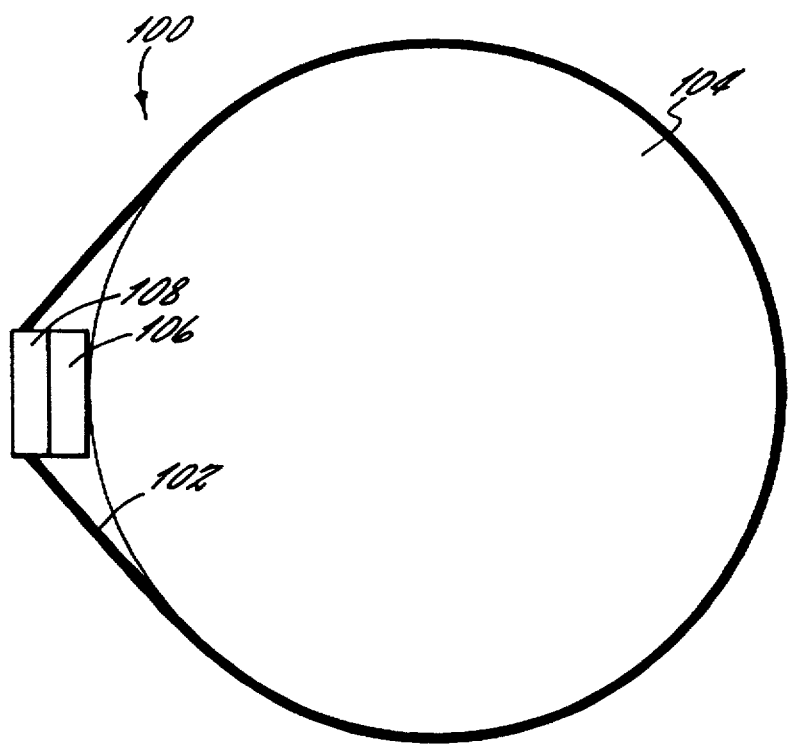
FIG. 1 illustrates a cerclage system according to various aspects of the present invention.

Referring now to FIG. 1, a cerclage system 100 according to various aspects of the present invention comprises a cable 102 for disposition around a bone 104; a retainer 108 for retaining cable 102; and a biasing mechanism 106 suitably configured for maintaining cable tension, after installation, such as due to slackening of cable 102. Cerclage system 100 is suitably implantable, such as into human tissue. System 100 may be used in conjunction with nearly any bone 104 or portion of bone, for example and solely by way of illustration, an approximately cylindrical bone such as a femur, humerus, radius, tibia, hip stem, or sternum. In addition, system 100 may be suitably adapted to any bone location or application, such as trochanteric reattachment or fixation of high tibial osteotomies. Bone 104 is depicted as circular in FIG. 1 for convenience of reference; however, it should be appreciated that bone 104 may be of any shape suitable for binding with cable 102.

Preferably, cable 102 is looped circumferentially around the exterior of bone 104 to maintain bone's 104 shape, position, and/or integrity. Accordingly, cable 102 may comprise any cerclage cable or wire now known or to be devised in the future, conventional or otherwise, of suitable strength and flexibility. For example, cable 102 suitably comprises a single wire. Alternatively, cable 102 may comprise a multistrand cable for added flexibility and strength. Further, cable 102 may comprise a relatively broad, flat band, such as a Parham band, or may comprise a suture. In accordance with a preferred aspect of the present invention, cable 102 comprises any suitable biocompatible material for implantation into biological tissue. For example, a suitable cable 102 comprises a multistrand cable comprising a bundle of individual fibers of biocompatible material, preferably of high tensile strength and flexibility, such as titanium alloy, cobalt chromium alloy, or stainless steel.

To retain bone's 104 shape and position, cable 102 is placed under tension. For example, after cable 102 is disposed around bone 104, cable 102 is tensioned using any suitable tensioning mechanism. For example, suitable tensioning tools include force multiplying pliers or screw thread activated spreading tools.

After cable 102 is disposed around bone 104 and placed under tension, in accordance with a potentially preferred aspect of the present invention, cable 102 is retained in a retainer 108. Retainer 108 is suitably configured to secure ends of cable 102 in relatively constant relation to each other. As so configured, retainer 108 preferably tends to prevent slippage of cable 102 which tends to reduce the tension in cable 102 and consequently induce slack. For example, referring now to FIGS. 2A–C, and in accordance with one aspect of the present invention, a suitable retainer 108 includes a crimp block 110 having two holes 112, suitably parallel, formed therethrough. Holes 112 formed in crimp block 110 are sufficiently large to receive the ends of cable 102 relatively freely. The ends of each hole 112 are suitably beveled to facilitate insertion of cable 102 into each hole 112. After cable 102 is suitably disposed around bone 104 and placed under tension, the ends of cable 102, disposed through holes 112 in crimp block 110, are secured, for example by crimping the sides of crimp block 110. Such crimping, while tension is maintained on cable 102, may be accomplished, for example, through the use of pliers. The normal action of the pliers serves to reduce the size of holes 112 thereby clamping the ends of cable 102 in position within crimp block 110. While retainer 108 thus described preferably comprises a crimp type retainer, it should be appreciated that retainer 108 may comprise any suitable mechanism for retaining the ends of cable 102 in position and substantially maintaining tension in cable 102 during retention.

In accordance with various aspects of the present invention, biasing mechanism 106 is suitably configured to dynamically maintain tension in cable 102 despite inadvertent loss of cable tension as may be caused by, for example, shifting of bone fragments or slipping of cable 102 in retainer 108. Biasing mechanism 106 operates in conjunction with bone 104 and is suitably responsive to tension in cable 102. For example, in accordance with a preferred aspect of the present invention, biasing mechanism 106 responds to a reduction in the tension in cable 102 and adds tension to compensate for slackening. Biasing mechanism 106 suitably includes a spring, a resilient material, or an analogous mechanism disposed between retainer 108 and bone 104, or alternatively, disposed in line with cable 102.

Figure 2A:
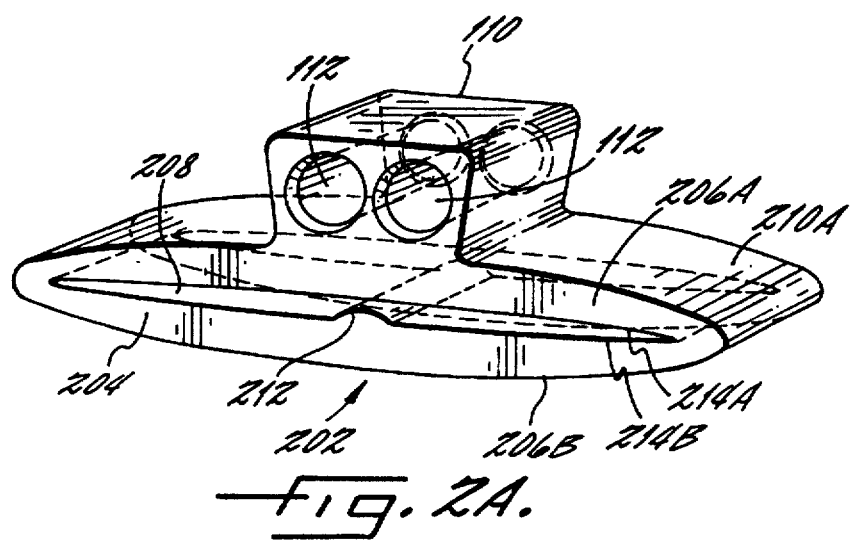
FIGS. 2A–C illustrate perspective, elevational, and top views, respectively, of an exemplary dynamically tensioning cable retainer for the cerclage system of FIG. 1.
Figure 2C:
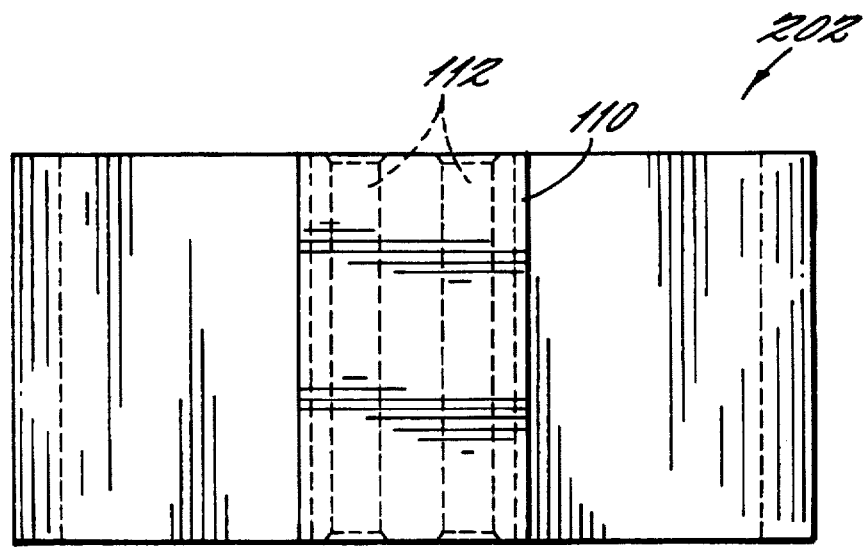
Figure 2B:
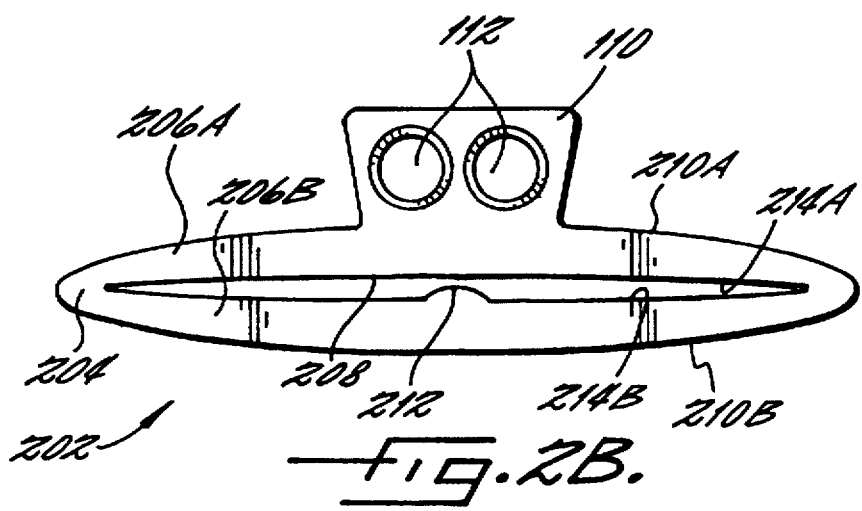

Referring to FIGS. 2A–C, in accordance with a first embodiment of the present invention, cerclage system 100 includes a spring 204 formed integrally with crimp block 110 to form a dynamically tensioning retainer 202. Retainer 202 is suitably formed of a durable, biocompatible material, such as cobalt chromium alloy, titanium alloy, stainless steel or the like. Retainer 202 suitably comprises crimp block 110, such as crimp block 110 described above, having first and second holes 112 formed therethrough and biasing mechanism 106, such as spring 204, formed integrally with crimp block 110. Spring 204 suitably comprises a leaf spring having, for example, two relatively stiff but resilient leaves 206A–B. Leaves 206A–B are suitably positioned substantially parallel to each other and joined at each end. Further, leaves 206A–B are preferably biased to curve in opposite directions, forming a space 208 between leaves 206A–B. In such a configuration of spring 204, when force is applied to outer surfaces 210A–B of leaves 206A–B, leaves 206A–B deform and partially collapse space 208 formed between leaves 206A–B. Conversely, as the force on outer surfaces 210A–B of leaves 206A–B is relieved, leaves 206A–B separate and return to their original configuration.

To maintain a desired minimum separation between leaves 206A–B, a spacer 212 is suitably disposed between leaves 206A–B. Spacer 212 may comprise any rigid or resilient material for maintaining separation between inner surfaces 214A–B of leaves 206A–B. For example, spacer 212 suitably comprises a semi-cylindrical protrusion formed in the inner surface 214B of lower leaf 206B. With such a configuration, as force is applied to the outer surfaces 210A–B of leaves 206A–B and the space 208 between leaves 206A–B collapses, inner surface 214A of upper leaf 206A abuts spacer 212, which in turn tends to prevent further collapse of leaf spring 204.

In accordance with this illustrated embodiment, spacer 212 may also serve as an indicator of appropriate tension. For example, the materials and configuration of leaf spring 204 may be selected to require a particular force, such as 100 pounds, on outer surfaces 210A–B of leaf spring 204 to collapse leaf spring 204 such that upper leaf 206A contacts spacer 212. Thus, when cable 102 is sufficiently tensioned to force upper leaf 206A into contact with spacer 210, the system communicates to the user (e.g., the surgeon) that the cable tension is placing 100 pounds of force onto leaf spring 204. With this parameter established, the tension on cable 102 may then be calculated.

Referring again to FIGS. 1 and 2A–C, retainer 202 preferably dynamically maintains tension in cable 102 disposed around bone 104. Initially, cable 102 is wrapped around bone 104 and retainer 202 is positioned on the surface of bone 104. Retainer 202 is suitably positioned such that outer surface 210B of lower leaf 206B abuts bone 104, and holes 112 in crimp block 110 are parallel to the plane of cable 102. The ends of cable 102, being suitably disposed through and retained in holes 112 in crimp block 110, are thus placed under suitable tension. As the tension is applied to cable 102, a corresponding force is applied to upper leaf 206A such that upper leaf 206A collapses toward lower leaf 206B abutting bone 104. Once the appropriate tension is applied to cable 102, leaf spring 204 suitably substantially completely collapses so that upper leaf 206A abuts spacer 212. Crimp block 110 is then crimped to hold cable 102 in position and substantially maintain tension on cable 102.

Figure 3:
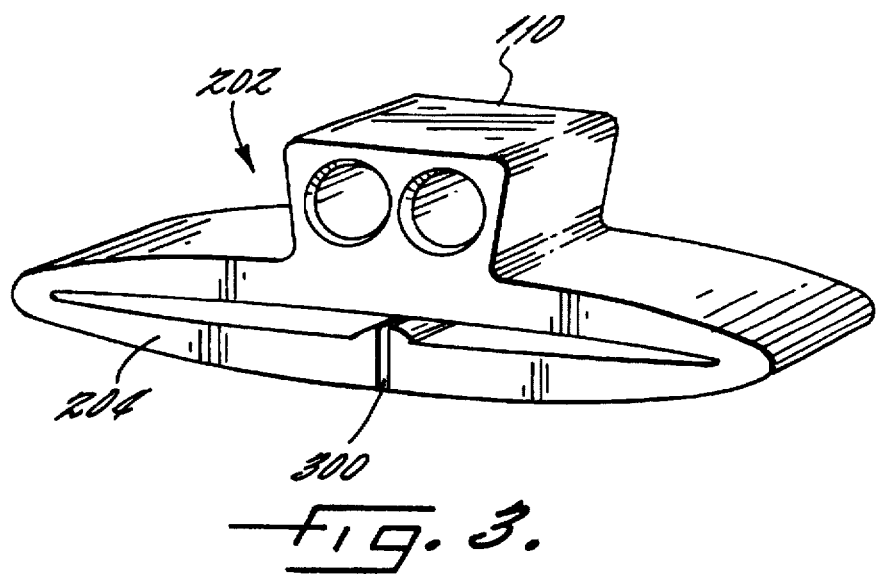
FIG. 3 illustrates one alternative embodiment of the cable retainer of FIGS. 2A–C having a slotted lower leaf.

In the event that cable 102 loses tension, for example due to shifting of bone fragments, retainer 202 maintains tension in cable 102. For example, and in accordance with a preferred aspect of this illustrated embodiment, as cable 102 slackens due to loss of tension, spring 204 pushes crimp block 110 away from bone 104, suitably with an approximate force according to a typical spring equation:

$$f = kx$$

where f is force exerted by spring 204, x is the displacement of crimp block 110 from its relaxed state, and k is the spring constant for spring 204. The spring constant is equivalent to the stiffness of spring 204. The spring constant may be varied to achieve different compression forces for different applications, for example by altering the materials and configuration of spring 204. For example, to achieve relatively low compression forces, lower leaf 206B may include a slot 300, as shown in FIG. 3, to facilitate collapse of space 208 with relatively low forces. In the embodiment, the outward force exerted by spring 204 tends to maintain tension in cable 102, even as slack develops in cable 102.

Figure 8:
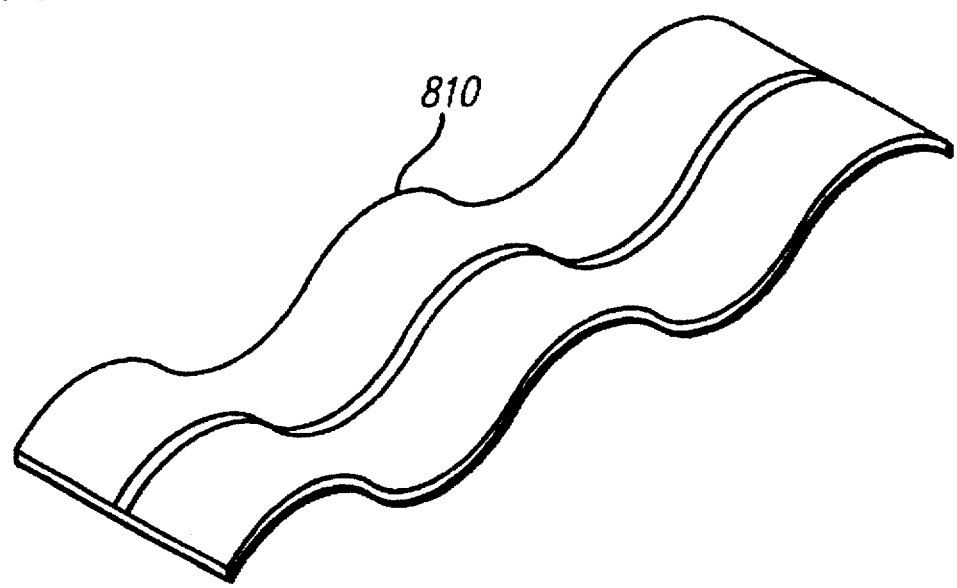
FIG. 8 illustrates an exemplary ribbon spring.

Other suitable biasing mechanisms 106 may be alternatively used instead of spring 204, as may be now known or hereafter devised by those skilled in the art. For example, a helical compression spring or a resilient material may be disposed between bone 104 and cable 102 or crimp block 110 to force cable 102 away from bone 104 and suitably maintain tension in cable 102. In addition, a ribbon spring, such as the ribbon spring 810 of FIG. 8, may be similarly disposed between bone 104 and cable 102 or crimp block 110 to suitably maintain tension in cable 102.

Figure 4:
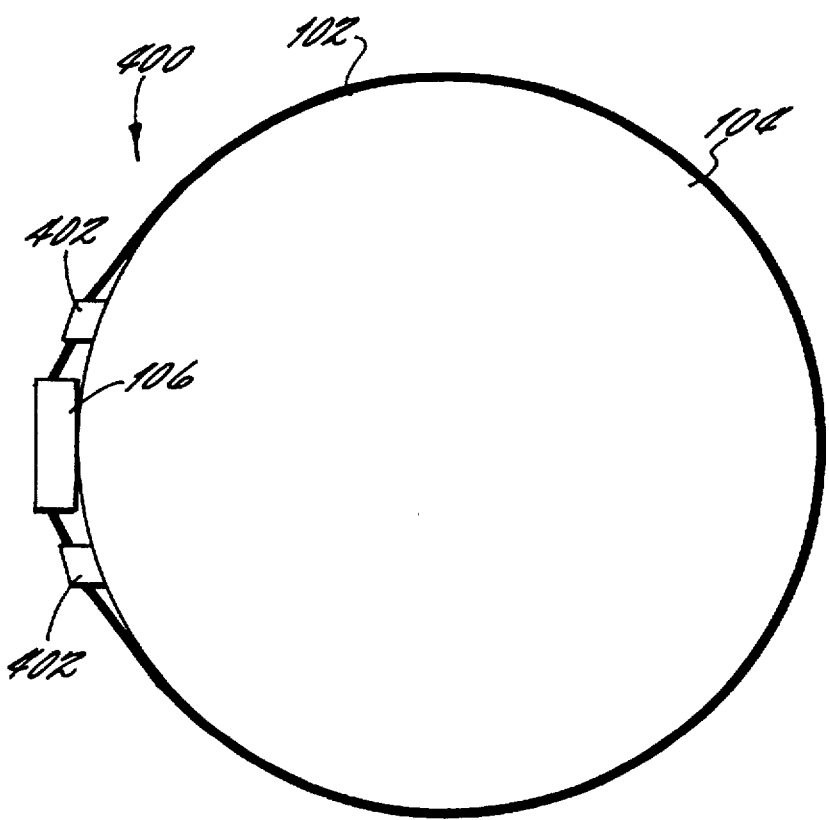
FIG. 4 illustrates a further alternative exemplary cerclage system using an in-line biasing mechanism.

In accordance with a further embodiment of the present invention, a suitable biasing mechanism 106 may be positioned in series with cable 102 to maintain tension. For example, referring now to FIG. 4, an alternative retainer 400 is suitably configured to dynamically tension and retain the ends of cable 102, for example with a pair of crimps 402, and includes a biasing mechanism 106 associated with crimps 402. Biasing mechanism 106 suitably comprises a high tension spring, such as a helical spring, leaf spring, Belleville spring, elastic material or the like. After cable 102 is disposed around bone 104 and tensioned, the ends of cable 102 are crimped within crimps 402. As slack develops in cable 102, biasing mechanism 106 contracts to pull cable 102 taut. The tension placed on cable 102 as biasing mechanism 106 contracts is suitably proportional, as described above, to the characteristics of biasing mechanism 106, such as the spring constant, and the displacement of the ends of cable 102 relative to each other.

Figure 5:
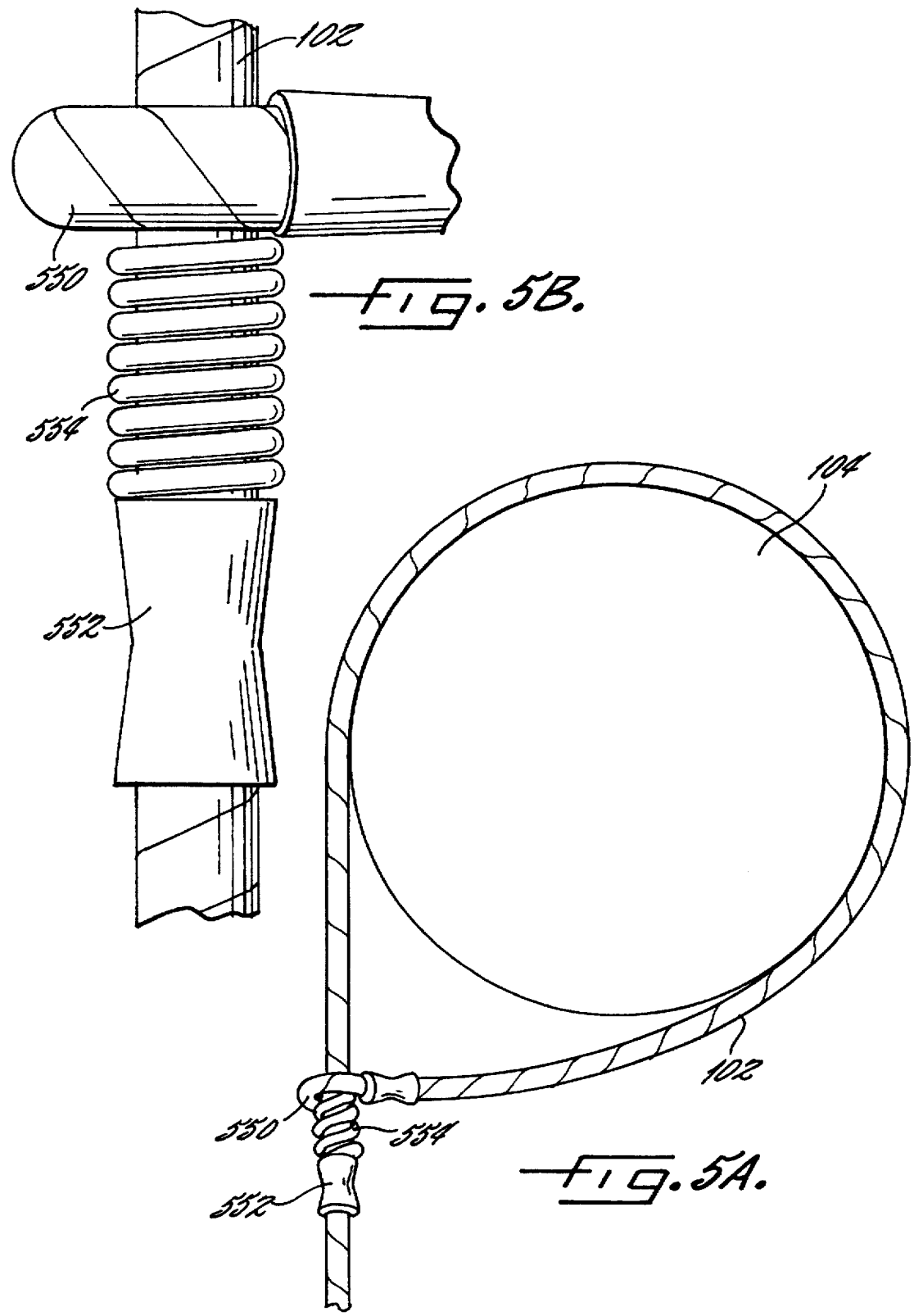
FIGS. 5A–B illustrate a further alternative exemplary cerclage system using an in-line biasing mechanism comprising a loop and a helical spring.
Figure 6:
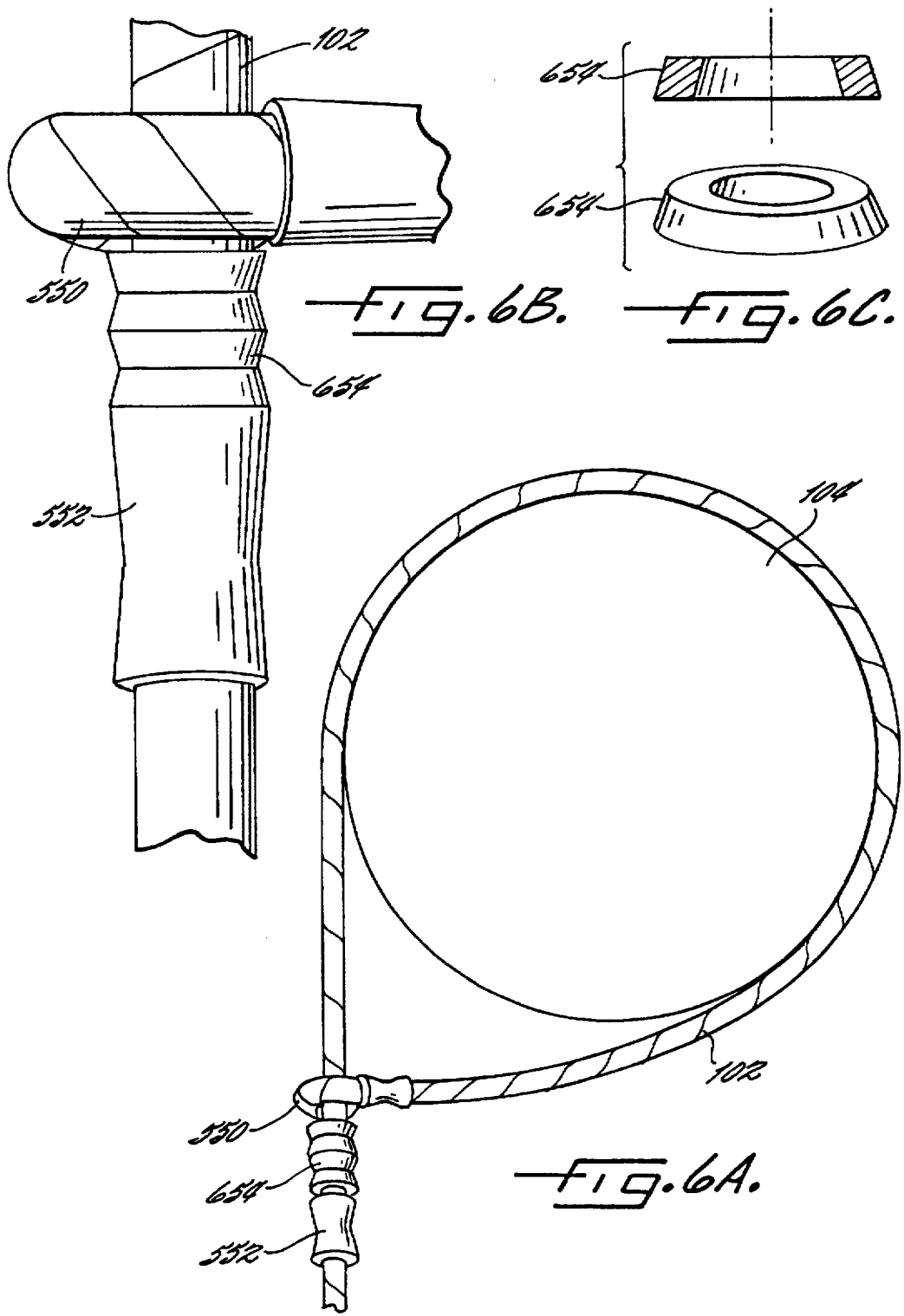
FIGS. 6A–C illustrate a further alternative exemplary cerclage system using an in-line biasing mechanism comprising a loop and a Belleville spring.

Alternatively, retainer 400 and biasing mechanism 106 may be configured separately. Referring now to FIGS. 5A–B, retainer 400 suitably comprises a loop 550 formed in one end of cable 102. The other end of cable 102 is wrapped around bone 104 and passed through loop 550. Retainer 400 further suitably includes block, for example a sleeve 552, fixed to cable 102, suitably by crimping or other appropriate mechanism, to prevent loop 550 from moving beyond the block. For example, sleeve 552 has a sufficient diameter to prevent loop 550 from passing over and around sleeve 552. Biasing mechanism 106 is suitably disposed to maintain tension in cable 102, for example between loop 550 and sleeve 552. Biasing mechanism 106 comprises any suitable biasing mechanism, for example a helical spring 554. Alternatively, biasing mechanism 106 may comprise a Belleville spring 654 (FIGS. 6A–C). Biasing mechanism 106 suitably biases loop 550 towards bone 104 and away from sleeve 552, thus tending to maintain tension in cable 102.

Figure 7:
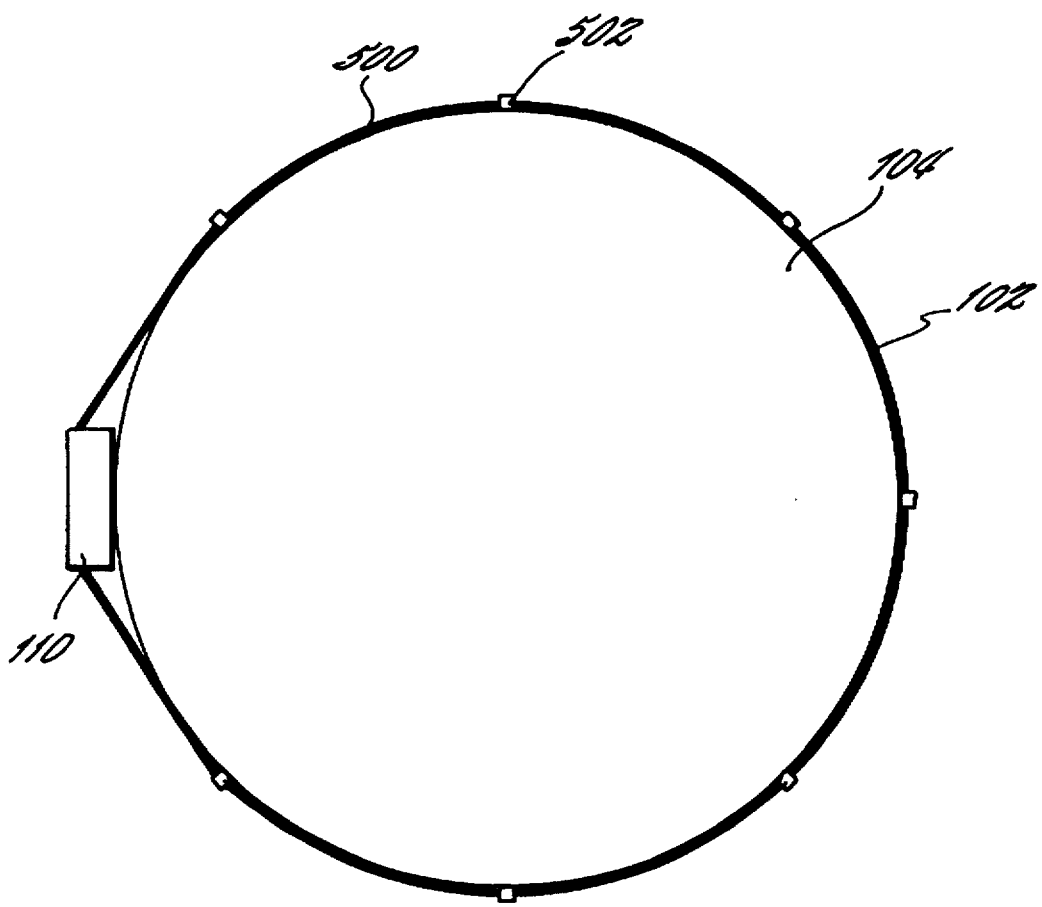
FIG. 7 illustrates a cerclage cable having a built-in biasing mechanism.

In yet another alternative embodiment of a system according to the present invention, biasing mechanism 106 is suitably incorporated into cable 102. Referring now to FIG. 7, in accordance with this embodiment, cable 102 suitably comprises respective multiple segments 500 connected by respective elastic joints 502. Cable segments 500 suitably comprise any high tensile strength, bio-compatible material, such as stainless steel cable, wire, or the like. Joints 502 comprise any suitable biasing mechanism, for example a resilient elastic material or a spring. Similarly, cable 102 may be entirely comprised of a resilient, elastic material. In accordance with this embodiment, after cable 102 is disposed around bone 104 and suitably tensioned, joints 502 or cable 102 expand according to the magnitude of the tension on cable 102. When the desired tension is achieved, the ends of cable 102 are fixed in position, for example with a crimp block 110. As cable 102 loses tension, for example due to shifting bone fragments, joints 502 or cable 102 tend to contract and maintain tension in cable 102.

In sum, a cerclage system according to various aspects of the present invention tends to dynamically tension and maintain cable tension in the presence of inadvertent or natural cable slippage or slackening. Biasing mechanism 106, disposed in line with cable 102 or between cable 102 and bone 104, provides supplementary tension to take up slack due to cable slippage. Further, biasing mechanism 106 may also serve to establish when a desired tension is achieved in cable 102.

While preferred exemplary embodiments of the present invention have now been made clear, there will be immediately obvious to those skilled in the art many modifications of structure, arrangements, proportions, the elements, materials and components, used in the practice of the invention which are adapted for a specific environment and operating requirements without departing from the scope of the invention as expressed in the appended claims.

We claim:

1. A cerclage retainer for retaining a cerclage cable, comprising:

a retaining block having a first hole and a second hole defined therethrough configured to receive the ends of the cable and fixedly retain the ends of cable therein; and a spring, including:
   a first leaf formed integrally with the retaining block; and
   a second leaf facing the first leaf, said second leaf having an inner surface and an outer surface, said outer surface being configured to engage the bone, wherein said leaf spring is configured to bias retaining block away from the bone.

2. The cerclage retainer of claim 1, further comprising a spacer formed on the inner surface of one of the leaves.

3. The cerclage retainer of claim 2, wherein the leaf spring is configured to compress so that the spacer contacts the other leaf when a predetermined force is applied to the leaf spring.

4. The cerclage retainer of claim 3, wherein the predetermined force is approximately 100 pounds.

5. The dynamically tensioning cerclage retainer of claim 1, wherein the second leaf includes a slot formed therein.

6. A cerclage system for disposition around a bone, comprising:

a cable configured to be disposed around the bone;

a retainer configured to retain the cable in substantially constant position; and a biasing mechanism, configured to be disposed between the retainer and the bone, responsive to tension in the cable for maintaining tension in the cable.

7. The cerclage system of claim 6, wherein the biasing mechanism includes a spring.

8. The cerclage system of claim 6, wherein the retainer and the biasing mechanism comprise a single unit.

9. The cerclage system of claim 8, further comprising a spring configured to abut the bone to bias the retainer away from the bone.

10. The cerclage system of claim 9, wherein the spring includes:

two leaves; and a spacer disposed between the leaves.

11. The cerclage system of claim 9 wherein the spring includes two leaves, wherein one at least of the leaves includes a slot formed therein.

12. A dynamically tensioning retaining system for retaining a cable disposed around a bone, comprising:

a retainer configured to be connected to the cable; and a biasing mechanism configured to be responsive to tension in the cable and configured to be connected to the cable for maintaining tension in the cable, wherein the retainer and the biasing mechanism are integrated into a single unit.

13. The dynamically tensioning retaining system of claim 12, wherein the retainer comprises a block.

14. The dynamically tensioning retaining system of claim 13, wherein the retainer further comprises a loop formed at the end of the cable and the other end of the cable is disposed therethrough.

15. The dynamically tensioning retaining system of claim 14, wherein the biasing mechanism is disposed between the block and the loop.

16. The dynamically tensioning retaining system of claim 15, wherein the biasing mechanism includes a helical spring.

17. The dynamically tensioning retaining system of claim 15, wherein the biasing mechanism includes a Belleville spring.

18. The dynamically tensioning retaining system of claim 12, wherein the biasing mechanism is configured to be disposed between the cable and the bone.

19. The dynamically tensioning retaining system of claim 12, wherein the biasing mechanism includes a ribbon spring.

20. The dynamically tensioning retaining system of claim 12, wherein the integrated retainer and biasing mechanism includes a leaf spring configured to bias the cable retained by the retainer away from the bone.

21. The dynamically tensioning retaining system of claim 20, wherein the leaf spring includes:

two leaves; and a spacer disposed between the leaves.

22. The dynamically tensioning retaining system of claim 20, wherein the leaf spring includes two leaves, wherein one at least of the leaves includes a slot formed therein.

23. The dynamically tensioning retaining system of claim 12, wherein the biasing mechanism is disposed in line with the cable.

24. The dynamically tensioning retaining system of claim 23, wherein the biasing mechanism comprises a leaf spring.

25. The dynamically tensioning retaining system of claim 23, wherein the biasing mechanism comprises an elastic component.

26. The dynamically tensioning retaining system of claim 25, wherein the elastic component is integrated into the cable.

27. The dynamically tensioning retaining system of claim 26, wherein the cable is comprised of elastic material.

28. The dynamically tensioning retaining system of claim 23, wherein:

the cable is comprises of a plurality of segments; and the biasing mechanism comprises at least one biasing component joining at least two of the segments of the cable.

* * * * *